(12) United States Patent
DeCamp et al.

(10) Patent No.: US 7,696,479 B2
(45) Date of Patent: Apr. 13, 2010

(54) METHOD AND APPARATUS FOR FREQUENCY-CONVERTING INFRARED LIGHT

(75) Inventors: Matthew F. DeCamp, Swarthmore, PA (US); Andrei Tokmakoff, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/446,588

(22) Filed: Jun. 2, 2006

(65) Prior Publication Data

US 2007/0018103 A1    Jan. 25, 2007

Related U.S. Application Data

(60) Provisional application No. 60/687,363, filed on Jun. 3, 2005.

(51) Int. Cl.
*G01J 5/02* (2006.01)

(52) U.S. Cl. .................................................. 250/339.06

(58) Field of Classification Search ............ 250/339.01, 250/339.02, 339.03, 339.04, 339.05, 339.06, 250/339.07, 339.08, 339.09, 339.1, 339.11, 250/339.12, 339.13, 339.14, 339.15
See application file for complete search history.

(56) References Cited

U.S. PATENT DOCUMENTS

| | | | | | |
|---|---|---|---|---|---|
| 3,530,301 | A | * | 9/1970 | Boyd et. al. ................... | 359/328 |
| 3,860,344 | A | * | 1/1975 | Garfunkel ....................... | 356/51 |
| 4,450,356 | A | * | 5/1984 | Murray et al. ........... | 250/339.11 |
| 4,980,566 | A | | 12/1990 | Heilweil | |
| 5,321,718 | A | * | 6/1994 | Waarts et al. ................. | 372/108 |
| 5,377,003 | A | * | 12/1994 | Lewis et al. .................. | 356/300 |
| 5,451,785 | A | * | 9/1995 | Faris ........................... | 250/330 |
| 5,563,508 | A | | 10/1996 | Tatah | |
| 5,682,397 | A | | 10/1997 | Scheps | |
| 5,717,209 | A | | 2/1998 | Bigman et al. | |
| 5,719,397 | A | * | 2/1998 | Hallett et al. ........... | 250/339.13 |
| 5,800,360 | A | | 9/1998 | Kisner et al. | |
| 5,912,910 | A | * | 6/1999 | Sanders et al. ................. | 372/22 |
| 6,108,081 | A | * | 8/2000 | Holtom et al. ............... | 356/301 |
| 6,347,014 | B1 | * | 2/2002 | Hayashi et al. ............. | 359/634 |
| 6,546,027 | B1 | | 4/2003 | Khaydarov | |
| 6,611,336 | B1 | * | 8/2003 | Walmsley et al. ........... | 356/450 |

(Continued)

FOREIGN PATENT DOCUMENTS

JP          10148856 A  *  6/1998

OTHER PUBLICATIONS

Hore et al., TI: Sapphire-based picosecond visible-infrared sum-frequency spectroscopy from 900-3100 cm<-1>, Applied Spectroscopy Soc. Appl. Spectrosc USA, vol. 58, No. 12, pp. 1377-1384, Dec. 2004.

(Continued)

*Primary Examiner*—David P Porta
*Assistant Examiner*—Kiho Kim
(74) *Attorney, Agent, or Firm*—Weingarten, Schurgin, Gagnebin & Lebovici LLP

(57) ABSTRACT

The invention relates to methods and apparatus for modifying the frequency characteristics of a spatially-dispersed mid-IR spectra for spectroscopy. In a preferred embodiment, sum frequency generation between a frequency-dispersed IR beam and an ultrafast optical pulse generates a spatially-extended optical signal that is collected with a CCD detector.

47 Claims, 7 Drawing Sheets

U.S. PATENT DOCUMENTS

| | | | |
|---|---|---|---|
| 6,798,507 B2 * | 9/2004 | Xie et al. | 356/301 |
| 6,830,345 B2 * | 12/2004 | Kamm et al. | 353/122 |
| 7,002,149 B2 | 2/2006 | Shigekawa et al. | |
| 7,256,885 B2 * | 8/2007 | Silberberg et al. | 356/301 |
| 7,356,053 B2 | 4/2008 | Khaydarov | |
| 7,501,627 B1 | 3/2009 | Herr | |
| 2003/0175160 A1 * | 9/2003 | Archibald et al. | 422/82.05 |
| 2004/0019282 A1 * | 1/2004 | Mullen et al. | 600/476 |
| 2004/0075840 A1 * | 4/2004 | Andersen et al. | 356/479 |
| 2004/0135086 A1 * | 7/2004 | Lewis et al. | 250/339.12 |
| 2004/0195511 A1 * | 10/2004 | Elmore et al. | 250/339.02 |
| 2006/0033923 A1 * | 2/2006 | Hirasawa et al. | 356/450 |

OTHER PUBLICATIONS

Van Der Ham et al., Self-dispersive sum-frequency generation at interfaces, Optics Letters, vol. 21, No. 18, Sep. 15, 1996.

Khalil et al., Coherent 2D IR spectroscopy: Molecular structure and dynamics in solution, J. Phys. Chem. A 2003, 107, 5258-5279.

Scarani et al., Four-photon correction in two-photon Bell experiments, Eur. Phy. J. D 32, 129-138 (2005).

Huttner et al., Photon-counting techniques for fiber measurements, Lightwave, Aug. 2000.

* cited by examiner

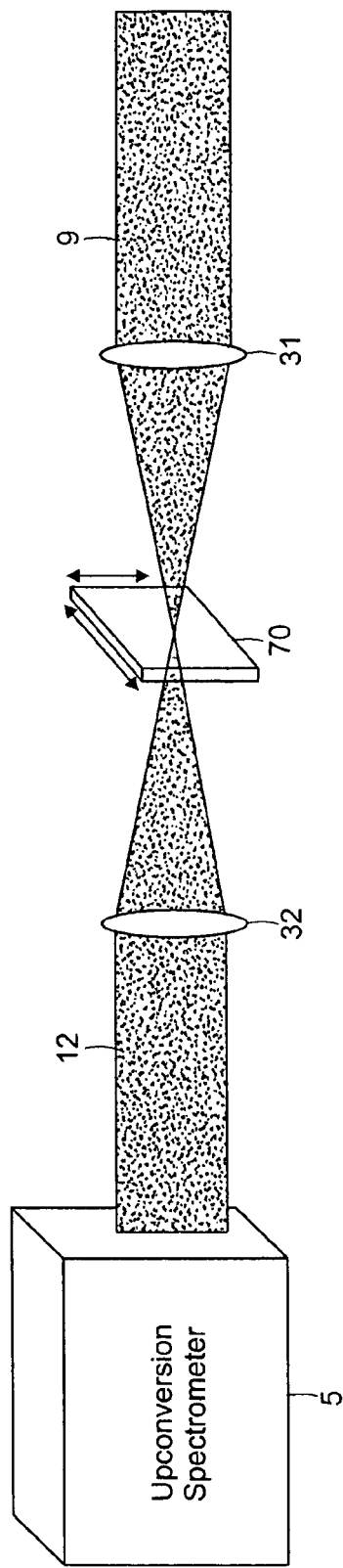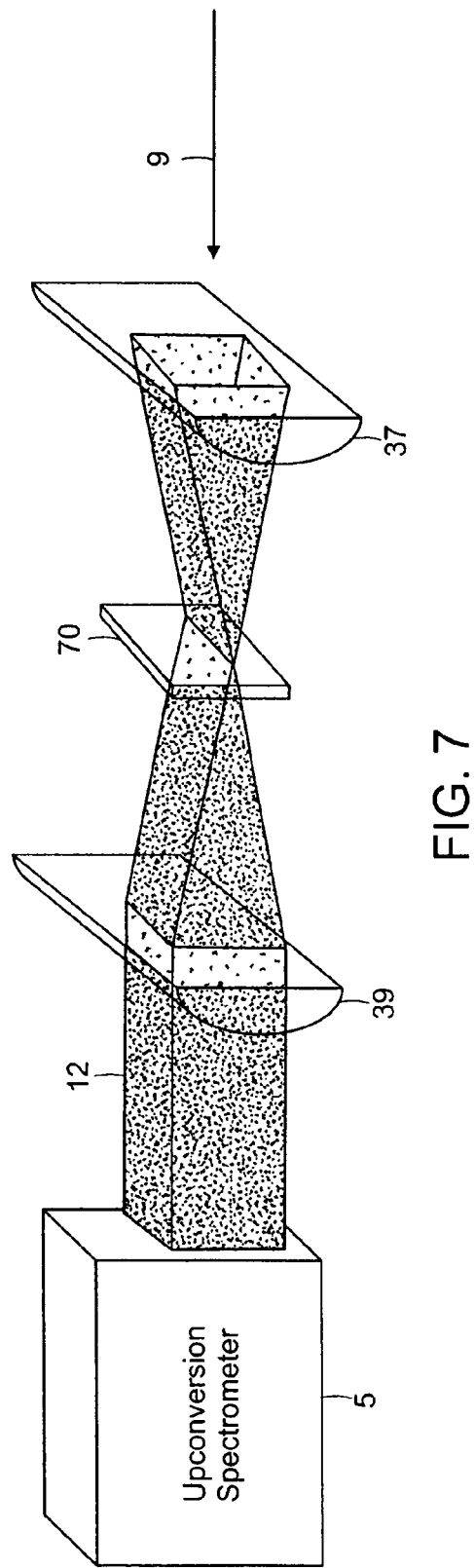

METHOD AND APPARATUS FOR FREQUENCY-CONVERTING INFRARED LIGHT

CROSS REFERENCE TO RELATED APPLICATIONS

This application claims priority under 35 U.S.C. §119(e) to provisional patent application Ser. No. 60/687,363 filed Jun. 3, 2005, the disclosure of which is hereby incorporated by reference.

STATEMENT REGARDING FEDERALLY SPONSORED RESEARCH OR DEVELOPMENT

N/A

BACKGROUND OF THE INVENTION

Time-resolved, infrared (IR) spectroscopy is an important tool in physical chemistry and condensed matter physics. It is also of use in trace gas detection and atmospheric chemistry. In particular, mid-IR vibrational resonances provide a method for probing of molecular structure that can be combined with time-resolved techniques to extract information on molecular dynamics.

Owing to interest in characterizing spectroscopic transients at multiple vibrational frequencies in femtosecond IR experiments, there has been a need for multichannel IR array detectors. However, these arrays are presently limited by their finite size (typically 32 to 128 elements in linear arrays), and by their high cost. Unlike CCD arrays, traditional IR arrays are also very sensitive to thermal blackbody radiation, making thermal isolation a prerequisite for imaging. Most mid-infrared detectors must be liquid nitrogen cooled to obtain adequate sensitivity. The use of inexpensive silicon charged-coupled-device (CCD) arrays could be advantageous, but the 1.1 micron bandgap of silicon has made CCD technology unable to directly detect mid-IR radiation.

The lack of suitable multi-channel IR detectors has caused researchers measuring transient absorption spectra in the mid IR (from 1000 to 4000 cm-1) to rely on, for example, scanning an independently tunable, narrowband, probe pulse or, alternatively, shifting a nanosecond broadband dye laser into the IR and then frequency-shifting it back into the visible for optical multichannel analyzer (OMA) detection.

However there continues to be a need for further improvements in infrared spectroscopy to more efficiently measure structures and/or dynamics of interest.

SUMMARY OF THE INVENTION

A preferred embodiment of the invention provides a method for altering the frequency of infrared light by generating an infrared light pulse, frequency-dispersing the light pulse by a grating or other dispersing element, generating an ultrafast second light pulse that is coupled to a common optical path with the first pulse that is directed into a frequency-conversion element, such as a nonlinear crystal, in order to generate a frequency-converted signal. The signal is then detected by a detector, such as a charge coupled device (CCD) or complementary metal-oxide semiconductor (CMOS) imaging detector. The detector provides spectral data to a data processor or computer for processing and display.

More generally, the invention further provides for an enhanced method of two dimensional (2D) IR spectroscopy applicable to investigating condensed phase molecular dynamics, transient chemical structures and structural vibrations through the measurement of vibrational couplings, energy shifts, and dipole orientations.

The invention further provides for a 2D IR spectrometer that frequency-converts a spatially-dispersed IR pulse using ultrafast optical pulsing capable of measuring transient molecular structures, vibrational couplings and dipole orientations.

A preferred embodiment of the invention provides for a method of detecting a spectrally dispersed mid-IR transient with a silicon CCD that makes use of ultrafast (femtosecond or picosecond) upconversion methods. A fast optical pulse is mixed with the spectrally dispersed IR pulse to generate a spatially dispersed SFG signal.

Another embodiment of the invention provides an apparatus for altering the frequency of a light pulse, comprising a first light pulse source, a first frequency-altering element, such as a grating, that is placed in the optical path of the first light pulse source, a second frequency-altering element, such as, for example a frequency-conversion element comprising a nonlinear crystal, and a second light pulse source that is combined with the first pulse prior to passing into the second frequency-altering element. One embodiment of the invention further provides for a detector that detects the frequency-shifted first light pulse. A further embodiment of the apparatus provides for the first light pulse to be an infrared pulse and the second light pulse source to be an optical pulse in the range under 10 picoseconds and preferably between 1 femtosecond and 10 picoseconds in duration. The invention further provides for an apparatus in which the frequency-conversion element is a non-linear crystal.

The invention provides a method for altering a light beam for spectroscopy by generating a first light pulse, frequency-dispersing the first light pulse by a grating or other dispersing element, generating a second light pulse that is coupled to a common optical path with the first pulse that is directed into a frequency-altering element, in order to generate a frequency-modified signal. The signal is then detected by a detector, such as a charge coupled device (CCD) or complementary metal-oxide semiconductor (CMOS) imaging detector.

BRIEF DESCRIPTION OF THE DRAWINGS

FIG. 6 illustrates a scanning 2D spectroscopic imaging device that is one embodiment of the invention, with rastering in the x and y dimensions.

FIG. 7 illustrates an embodiment comprising a scanning 2D spectroscopic imaging device that employs line-imaging to obtain spectral and spatial information simultaneously.

DETAILED DESCRIPTION OF THE INVENTION

The method and apparatus of a preferred embodiment of the invention disclosed herein uses a solid-state nonlinear crystal to upconvert an infrared laser pulse followed by optical detection. Narrowband infrared, probe-pulse detection, employing spectrographs and optical detectors, is useful for observing transient energy transfer, molecular structural rearrangement, and other chemical and physical processes. Such detection schemes can be used to obtain molecular transient absorption spectra in the visible by picosecond or femtosecond continuum pulse-generation. Enhancing methods for detecting and analyzing spectral characteristics of IR pulses is also useful for studying materials and component capabilities and signal transmission in telecommunications networks.

A preferred embodiment uses nonlinear optical mixing techniques, such as sum frequency generation (SFG), to provide an efficient method of "upconverting" mid-IR radiation to the visible, allowing a silicon-based detector to become a viable alternative to standard IR detectors. The upconversion technique uses SFG between a broadband optical pulse and a narrowband IR pulse to generate an optical signal. Provided that the broadband laser intensity is constant, the SFG intensity is proportional to the narrowband IR intensity. Such upconversion methods are useful for analytical chemistry, thermal imaging, trace-gas detection, analyzing telecom spectra and ultrafast laser characterization, for example.

Upconversion of an infrared spectrum onto one dimension on an IR array and a spatial coordinate (x) in the other dimension can be used to give a linear image of a sample with chemical specificity. If this is coupled with a spatial scanning of the orthogonal dimension (y) one can extend this method to chemically sensitive imaging of a two-dimensional area of a sample region. Certain geometric configurations can encode along an axis of spectral dispersion of a first light pulse a spatial location of a probe pulse that is focused at a sample plane.

Figure 1:
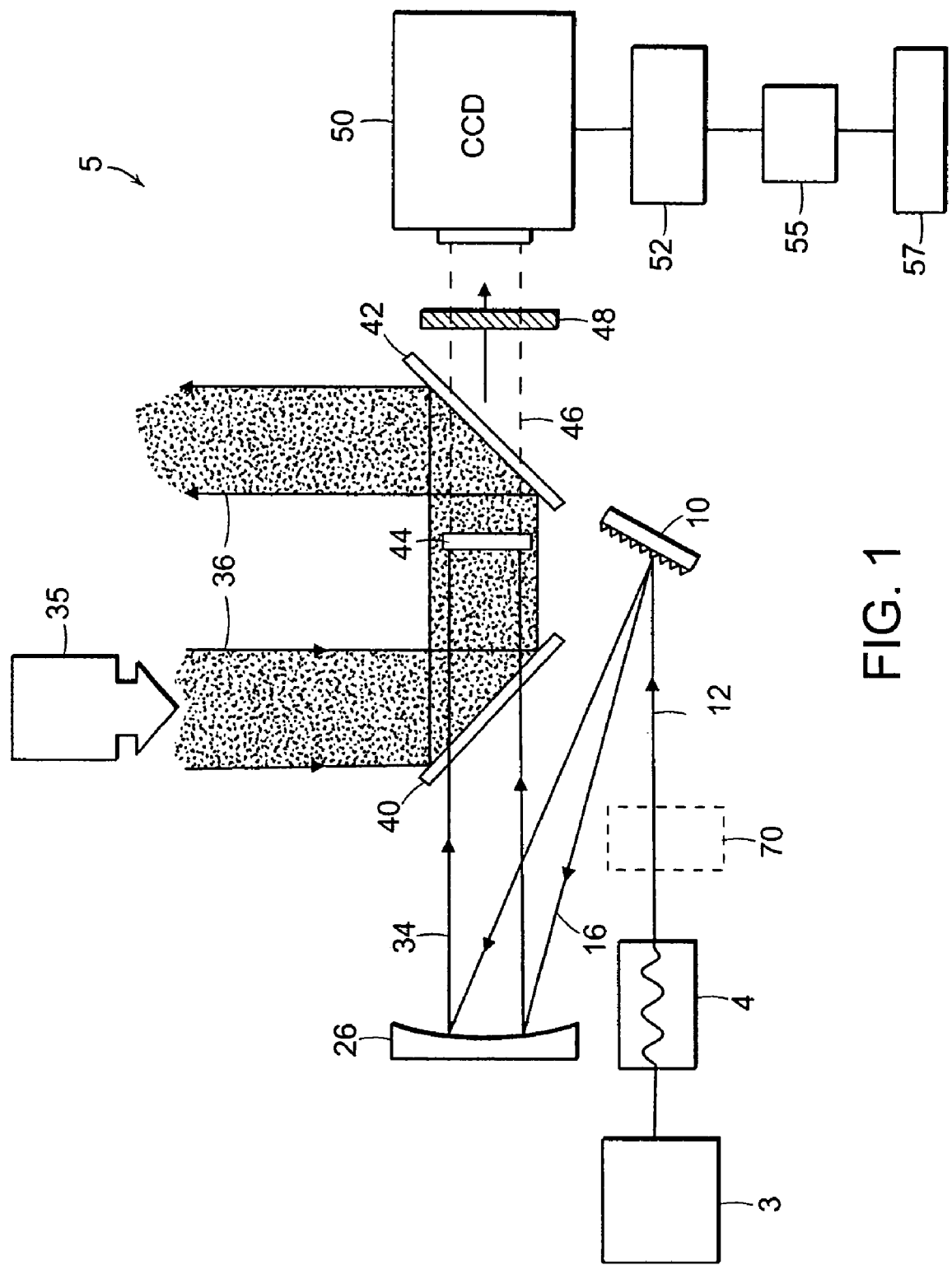
FIG. 1 illustrates a preferred embodiment of an apparatus in accordance with the present invention.

Referring to FIG. 1, details of a preferred embodiment of the invention are presented in the form of an upconversion infrared spectrometer 5. A femtosecond optical pulse 36 is mixed with a spectrally dispersed IR pulse 34 to generate a spatially dispersed SFG signal 46. The upconversion method has several technical challenges in implementation. In this case, the optical pulse 36 is temporally short such that optical fluences of $\mu J/cm^2$ will achieve good SFG efficiency. This is one of the important advantages of the invention, where previous methods have required greater optical fluences. The SFG signal 46 is collected by a CCD imaging device or video camera 50. The frequency resolution and bandwidth of this technique are only limited by the optical components, not the input laser characteristics. With simple optical components, this method can be a relatively inexpensive alternative to traditional IR array detectors.

The input IR light 12 is generated from a first light source 3, including a 1 kHz optical parametric amplifier 4 (OPA), pumped by an IR laser, including, for example, a 150 μJ, 80 fs, 800 nm laser pulse from an amplified Ti:Sapphire laser, and the spatially-dispersed form of this IR light pulse 34 is mixed with light from a second sub-picosecond light source 35, for example with an unfocused 40 μJ, 80 fs, 800 nm laser pulse source. The OPA 4 can be centered at 2620 $cm^{-1}$ with a working bandwidth of ~120 $cm^{-1}$. The focusing resolution of the dispersed IR pulse 34 is ~230 μm.

A preferred embodiment of the present invention succeeds in combining an ultrafast optical pulse with a mid-IR pulse that has already been frequency-dispersed. An important advantage of this method is that the intensity of the optical pulse is kept high (because decreasing the length of the pulse increases its peak power) in order to increase conversion efficiency.

A preferred embodiment employs a planar dispersive diffraction grating 10 with 150 grooves per millimeter. It will be appreciated by one skilled in the relevant art that other gratings and other types of frequency dispersion devices can be employed, such as, for example, a prism or a transmissive grating; however, a planar dispersive diffraction grating is most preferable for working in the mid-IR region of one preferred embodiment. The spectrometer apparatus 5 of this embodiment further includes a 25 cm focal-length metal mirror 26 optically coupled to the grating 10.

Figure 2:
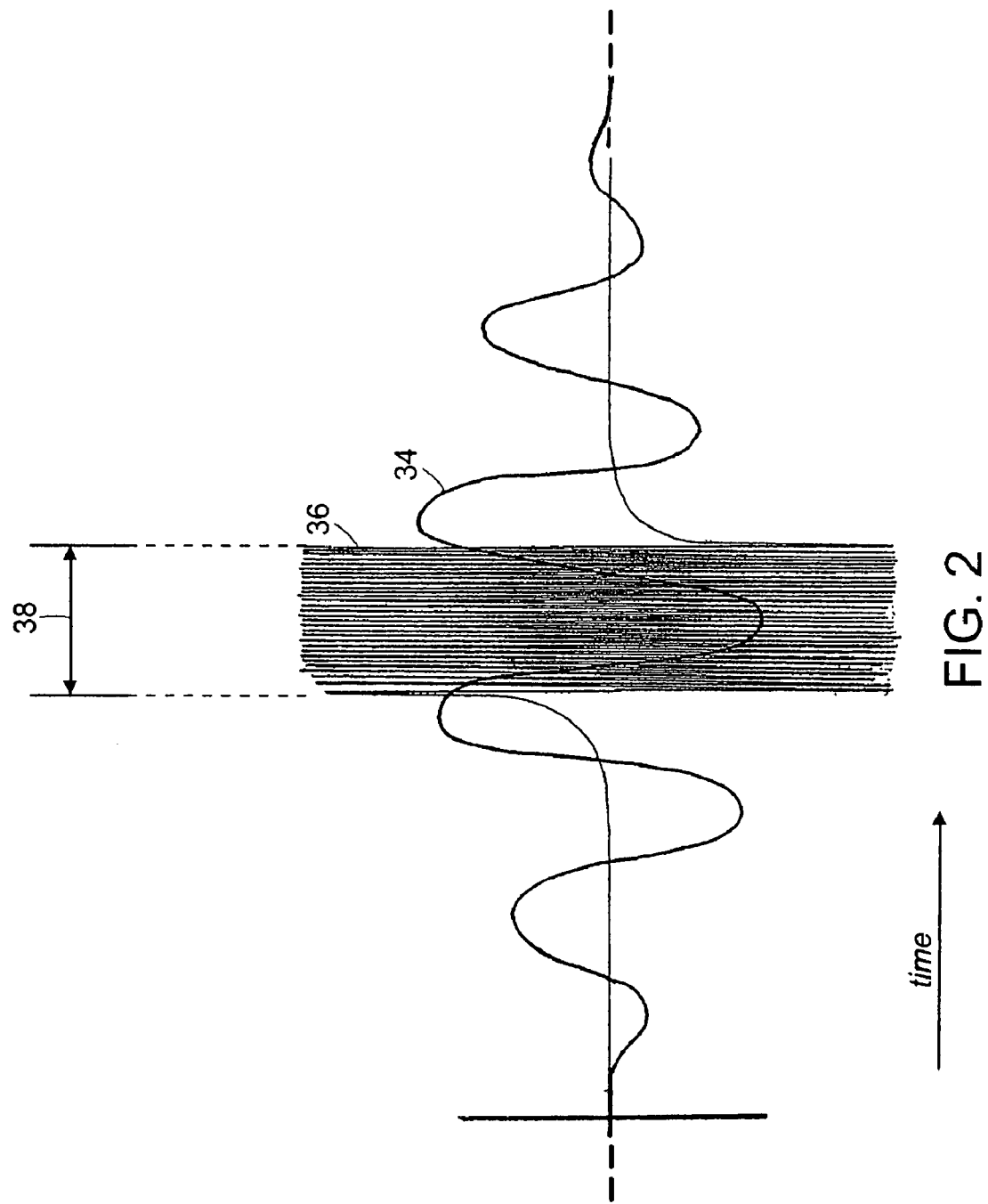
FIG. 2 is a schematic depiction of an ultrafast higher-frequency light pulse combining with a lower frequency light pulse.

Turning briefly to FIG. 2, the spatially-dispersed wavelengths 16 are collectively depicted schematically as a single, spatially-dispersed and frequency-dispersed, first light pulse 34. The spatially-dispersed light pulse 34 is overlapped in a common optical path by a second higher-frequency light pulse 36. The pulse duration 38 in the preferred embodiment is ultrafast, for example, 80 femtoseconds (fs), with many cycles of the second higher-frequency light pulse 36 overlapping less than one cycle of the first spatially-dispersed, lower-frequency, mid-IR light pulse 34.

Referring again to FIG. 1, in one embodiment, at the focal plane of the spectrometer there can be positioned an SFG crystal 44, which can be a Type I 8×8×1 $mm^3$ $KNbO_3$ crystal cut at 41 degrees, although it should be appreciated by one skilled in the art that a variety of Type 1 or Type 2 crystals can be similarly employed. In the embodiment, <200 nJ and 40 $cm^{-1}$ of the IR light 34 spans the crystal face, easily within the phase-matching condition of the $KNbO_3$ crystal 44. Before the spectrometer focal plane, a $CaF_2$ window coated to reflect 800 nm is positioned and used as a dichroic beamsplitter 48. The second light pulse 36 illuminates the entire crystal surface. The polarization of the optical pulse is controlled by a half-wave plate, and is set to maximize the SFG signal.

The configuration of the optical path, whereby the dispersive element (e.g., grating 10 in one preferred embodiment) sits prior to the SFG crystal, is important to the frequency resolution. By spatially dispersing the IR pulse prior to upconversion pumping, the SFG occurs over the full areal extent of the crystal surface, thereby enabling detection of the upconverted light along the entire bandwidth of the IR pulse.

That the pulse 36 be ultrafast is important to the results, because the shorter timed pulse allows greater intensity to be achieved for the same energy input and areal extent of the pulse. The relationship of intensity to energy, time and area is as follows:

Intensity=(energy/time)/area

Thus, also, by reducing the time of the pulse, a greater spatial area can be illuminated for any given energy and intensity. This means that a spatially-dispersed beam engaging a larger areal extent of a non-linear SFG crystal 44 can be upconverted more efficiently. While any ultrafast pulse 36 in the femtosecond to nanosecond range can be used for pumping, a pulse shorter than or equal to ten picosecond is preferable. As previously described, the preferred embodiment employs an 80 femtosecond pulse.

The SFG signal 46 is peaked at a wavelength that is the arithmetic sum of the IR frequency and the ultrafast optical pulse frequency and is only generated in locations where both the IR and visible light interact. In a preferred embodiment the SFG signal 46 is peaked at ~655 nm. The resulting SFG signal 46 has one spatial dimension containing the IR spectral content 34 and another representing the focusing conditions of the incident IR beam 12. To ensure good SFG efficiency, the IR pulse 34 and optical pulse 36 must be temporally overlapped. Because the IR pulse is spectrally dispersed, the results are relatively insensitive to the relative timing between the IR pulse 34 and the 800 nm pulse 36. This is one of the advantages of the invention.

The upconverted intensity is proportional to the product of the IR and visible pulse intensities. However, it is most preferable that the optical beam 36 have a flat spatial profile across the crystal 44 to ensure a flat spectral response for the IR pulse 34. The thickness of the nonlinear crystal 44 will also limit the bandwidth (not resolution) that can be up-converted on a single shot. For example, IR bandwidths larger than 100 cm$^{-1}$ can require crystal thicknesses less than 300 µm.

In the preferred embodiment of the invention, the SFG signal 46 is imaged directly onto the CCD array 50, which is a Watec LCL-902C monochrome CCD camera. The quoted sensitivity of the camera 50 is 0.01 lux and the area is 8.4(H)× 9.8(V)mm$^2$. Given the 30 fps frame rate of the camera 50, a single count on the camera corresponds to ~100 visible photons. Each video frame is captured by a video capture board computer interface 52, for example a video capture board National Instruments NI-1407 video capture board, retrieving 640(H)×480(V) pixels with 8-bit resolution. With the input parameters described above, the signal is easily visible to the naked eye and saturates the CCD camera 50.

A dielectric high-reflecting mirror 42 for 800 nm and a 650 nm bandpass filter 48 is used to isolate the SFG signal 46. The beam is attenuated with a neutral density filter, which in the preferred embodiment is also part of filter 48, reducing the SFG signal by a factor of ~20 prior to the camera 50. The 230 µm focusing spotsize corresponds to about 28 horizontal and 24 vertical pixels, resulting in ~25 distinct frequency channels. To collect a one-dimensional spectrum, the video frame is integrated or binned along the vertical dimension resulting in a typical signal to noise ratio of greater than 40:1 (~10 mOD) per video frame. A commercial CCD line camera, synchronized to the pulsed laser, provides for single shot measurements. If required, further SFG signal amplification can be achieved by increasing the incident 800 nm intensity of the upconversion pulse 36, either by using a shorter pulse or increasing the pulse energy.

Also shown in FIG. 1, the invention further provides for an image processor computer 55 configured to receive and process signals from the video capture board computer interface 52. In a preferred embodiment, a display 57 is connected to receive information from the image processor computer 55.

Figure 3:
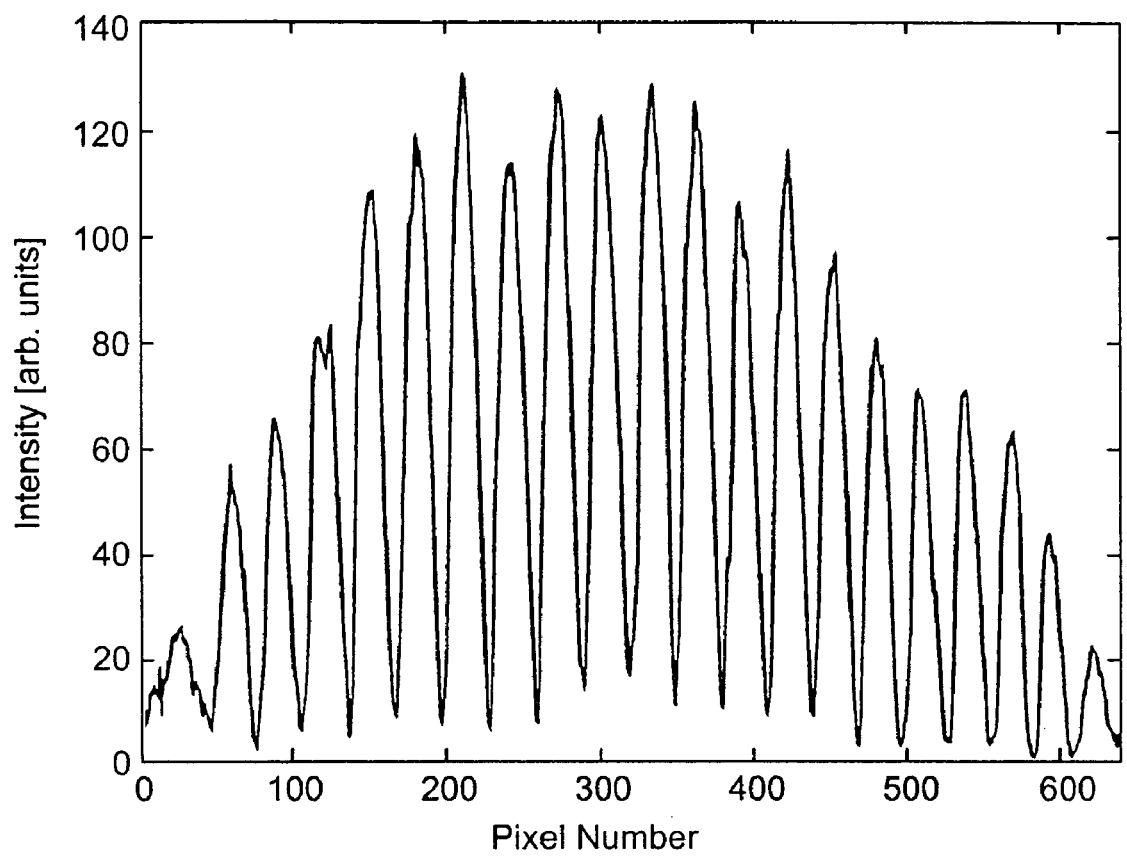
FIG. 3 illustrates an upconverted spectral interferometry of an IR pulse train.
Figure 4:
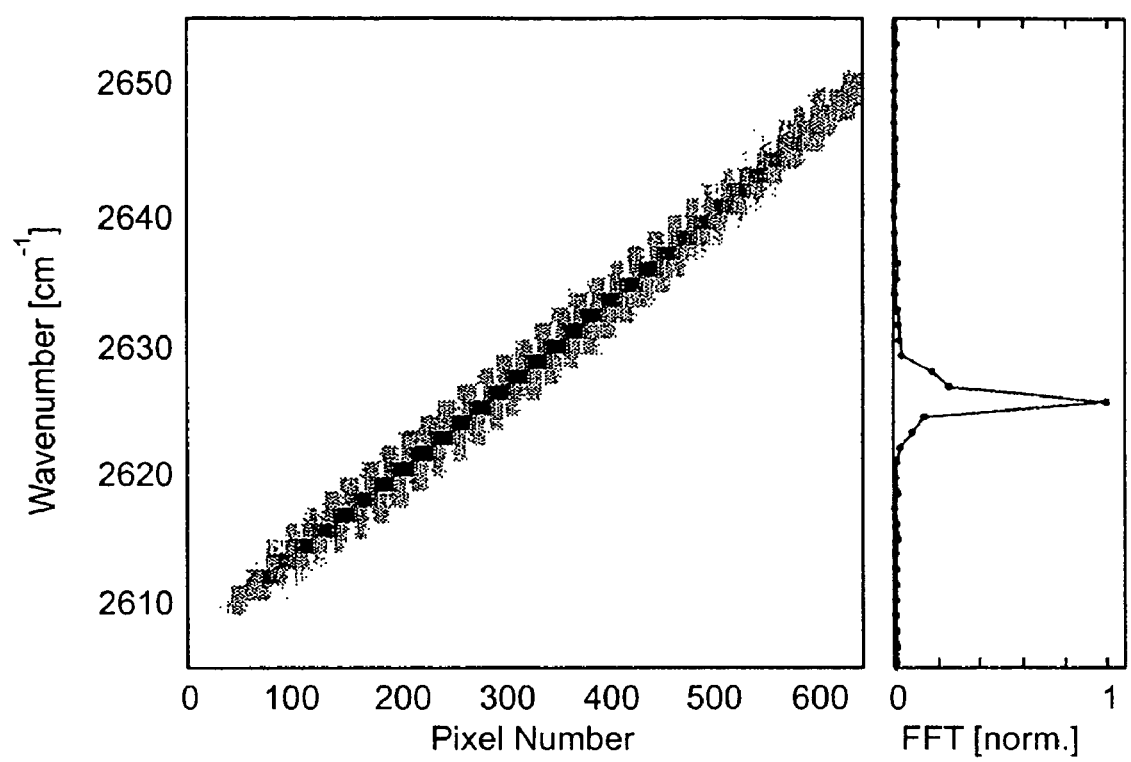
FIG. 4 illustrates a frequency calibration of the CCD array juxtaposed with a Fast Fourier Transform of one of the pixels.

During a calibration procedure to characterize the spectrometer, the source 3 may be a spectral interferometer. Referring now to FIG. 3, in the preferred embodiment calibration of the spectrometer 5 is performed using a Michaelson interferometer to generate two identical IR pulses. The time delay between the two pulses is controlled by a calibrated motorized delay line. The pulse train is sent into the SFG spectrometer and the resulting spectra are recorded as a function of pulse separation (FIG. 3). The temporal interferogram of each CCD pixel is Fourier transformed, resulting in the frequency calibration for each pixel (as shown in FIG. 4).

The position and width of the calibration surface gives the frequency calibration and resolution of the spectrometer 5. As seen in FIG. 4, the stepwise pattern in the pixel calibration is a consequence of the discrete Fast Fourier Transform (FFT). The average width of the FFT provides the frequency resolution of 1.81±0.03 cm$^{-1}$. The slope of the calibration surface results in a pixel calibration of 0.0666 cm$^{-1}$ pixel.

Figure 5:
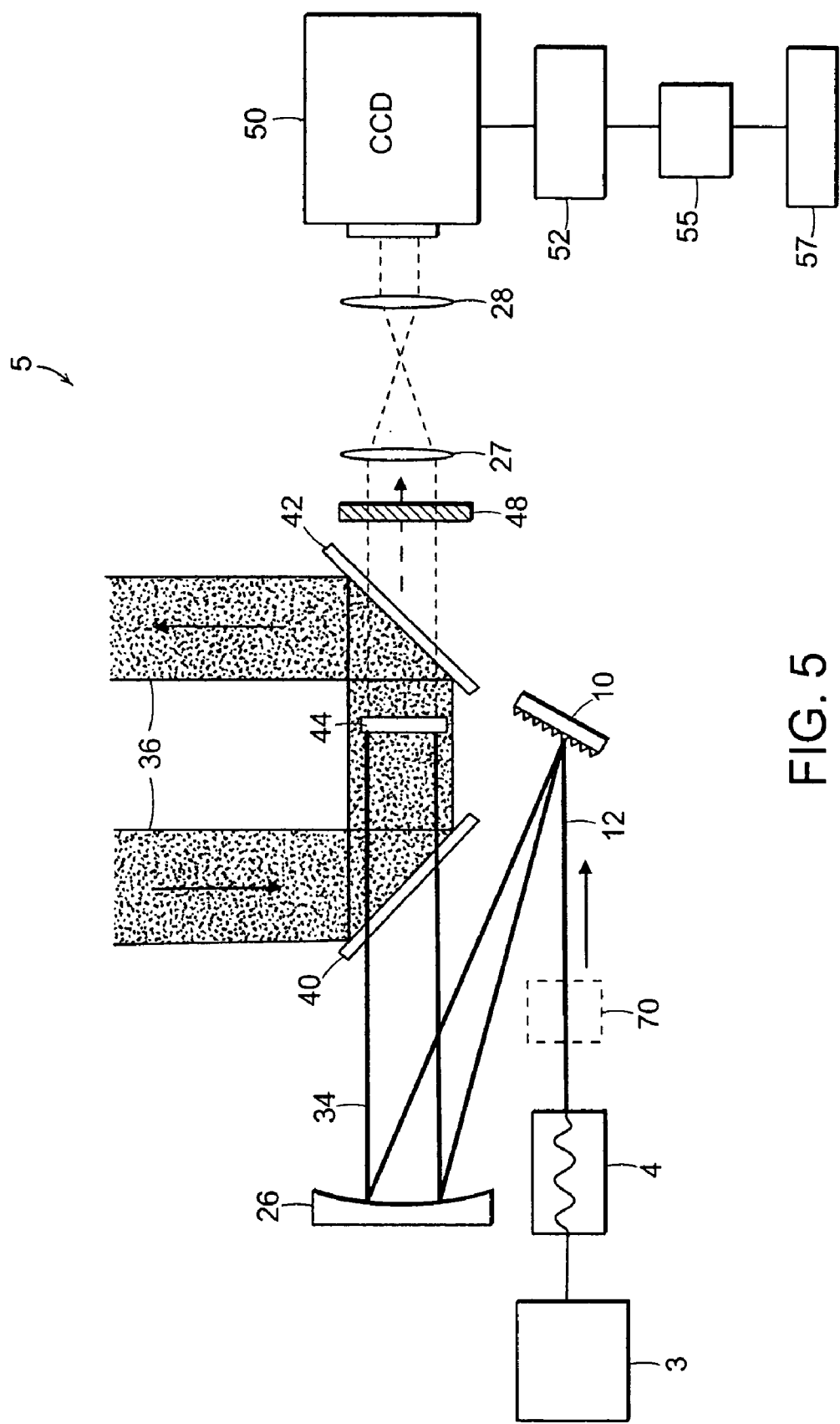
FIG. 5 illustrates an embodiment of the present invention employing telescopic lenses for tighter focusing.

Referring again to FIG. 1, owing to the extended Rayleigh range of the IR beam 34, the emitted SFG signal 46 is effectively collimated; and thus no other optical focusing elements are necessary prior to detection. When using tighter focusing optics, a simple optical telescope can be used to image the SFG signal 46 onto the CCD array 50. FIG. 5 illustrates positioning of telescope lenses 27 and 28 in one such embodiment, where the other numbered elements of FIG. 5 correspond to similarly numbered elements in FIG. 1.

The theoretical instrument frequency resolution of the spectrometer 5, dictated by the focal spotsize (in turn dictated by the f-number of the lenses 27 and 28 in FIG. 5) and grating 10, is 1.83 cm$^{-1}$, implying that the frequency resolution of the spectrometer is only limited by the optics. Reductions in the f-number of the system (i.e., focusing tighter) or increases in the groove density of grating 10 by a factor of two can improve the frequency resolution accordingly. Reduction in the f-number will also effectively increase the number of useable spectrometer channels.

While the CCD array 50 can measure single spectra easily, multiple independent spectra can also be taken simultaneously without any additional optical components. Multiple independent IR beams 12, 34, vertically (or horizontally) displaced, can be inserted into the spectrometer 5. The resultant SFG signal 46 has multiple distinct stripes separated vertically (or horizontally).

Given the focusing resolution, twenty independent spectra can be acquired simultaneously with the CCD array of the preferred embodiment. This ability to acquire multiple spectra simultaneously enables spectroscopic imaging. For example, a spectrally dispersed pulse can be projected onto a sample so that independent spectra are spatially displaced along the sample.

Generally, the invention further provides an optional method for studying properties of a sample 70, which is shown positioned in the optical path in FIG. 1. One skilled in the art will appreciate that a sample 70 to be investigated by the method and apparatus of the invention can be placed many alternate locations along the primary optical path of the primary IR probe beam, depending on the specific, sample interactions that are the subject of study. Here, the word "sample" is to be construed most broadly, to include any material, composition, mixture, object, liquid, solid, plasma, volume or other subject matter to be studied, analyzed, monitored, investigated, or otherwise detected by the spectrometer 5. By way of example and without limiting the numerous subject areas of application, such detection includes such subjects as:

time evolution of liquid interactions;

vibrational couplings from H-bonding, H—C bonding, C—O bonding and other molecular bonding interactions;

amide transitions to understand the structural basis for collective amide vibrations in model peptides and for other secondary and tertiary protein structures;

structural variations in biomolecules, in order to further describe the state of denatured proteins, or within living cells;

optical communication signals and the spectral characteristics of optical telecommunications transmissions and/ or signals, of telecom network components, and fiberoptic materials; and, inter alia, environmental monitoring and detection, remote sensing, and/or subjects of night-vision applications.

In a further embodiment of the disclosed invention, a scanning 2D spectroscopic imaging device as shown in FIG. 6 comprises a first objective lens 31 used to focus an IR probe beam 9 to probe microscale and nanoscale sample(s) 70 and transmit a signal beam 12 through second objective lens 32, the resulting signal beam 12 to impinge upon the upconversion spectrometer 5. In this case, the sample 70 is rastered in the x and y dimensions such that the entire sample 70 is probed by the incoming IR light 9. After the sample 70 the transmitted light 12 is collected and sent to upconversion spectrometer 5 for spectral analysis. The spatial resolution is given by the focusing optics, and can be as fine as about two microns. This geometry can also be inverted, such that the IR light 9 is reflected (scattered) off the surface of sample 70 and collected by the upconversion spectrometer 5.

In yet another embodiment of the invention, a scanning 2D spectroscopic imaging device as shown in FIG. 7 comprises a first objective lens 37 used to focus an IR probe beam 9 to probe microscale and nanoscale sample(s) 70 and project through second objective lens 39 the resulting signal beam 12 to impinge upon the upconversion spectrometer 5. In this case, the sample is line-imaged in the x-dimension using a cylindrical lens 37. The transmitted radiation 12 is then collected by another cylindrical lens 39 and sent into the upconversion spectrometer 5. Similarly, for example, the spatial location of the probe pulse can be encoded along the x-axis (horizontal) at the sample, which x-axis can be aligned with the frequency dispersion axis of frequency-dispersed pulse.

Referring again to FIG. 7, in one embodiment of this configuration, because the spectrometer 5 includes a 2D array, one dimension of the array is wavelength, while the other dimension is the spatial x-dimension, thus obtaining spatial and spectral information simultaneously. If the x-dimension is the horizontal, then the vertical dimension can encode the probe pulse frequency, depending on the specific geometric configuration, the vertical dimension can encode the frequency of probe pulse 9 if frequency-altering element 44 is a grating having a dispersive axis orthogonal to the dispersive axis of grating 10.

In yet another embodiment, this method is adapted to image a full x-y spatial map by rastering the sample along the y-axis. Again, the spatial resolution of this method can be as fine as about two microns.

Figure 8A:
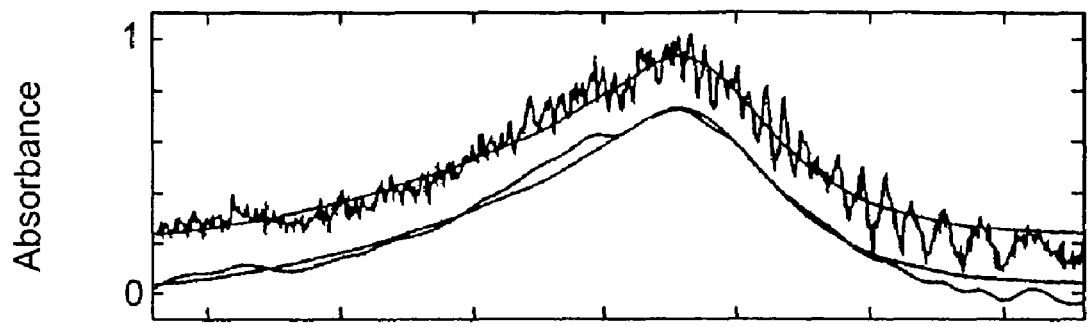
FIGS. 8($a$) and 8($b$) illustrate the output of one embodiment of the invention comprising a dual channel spectrometer.
Figure 8B:
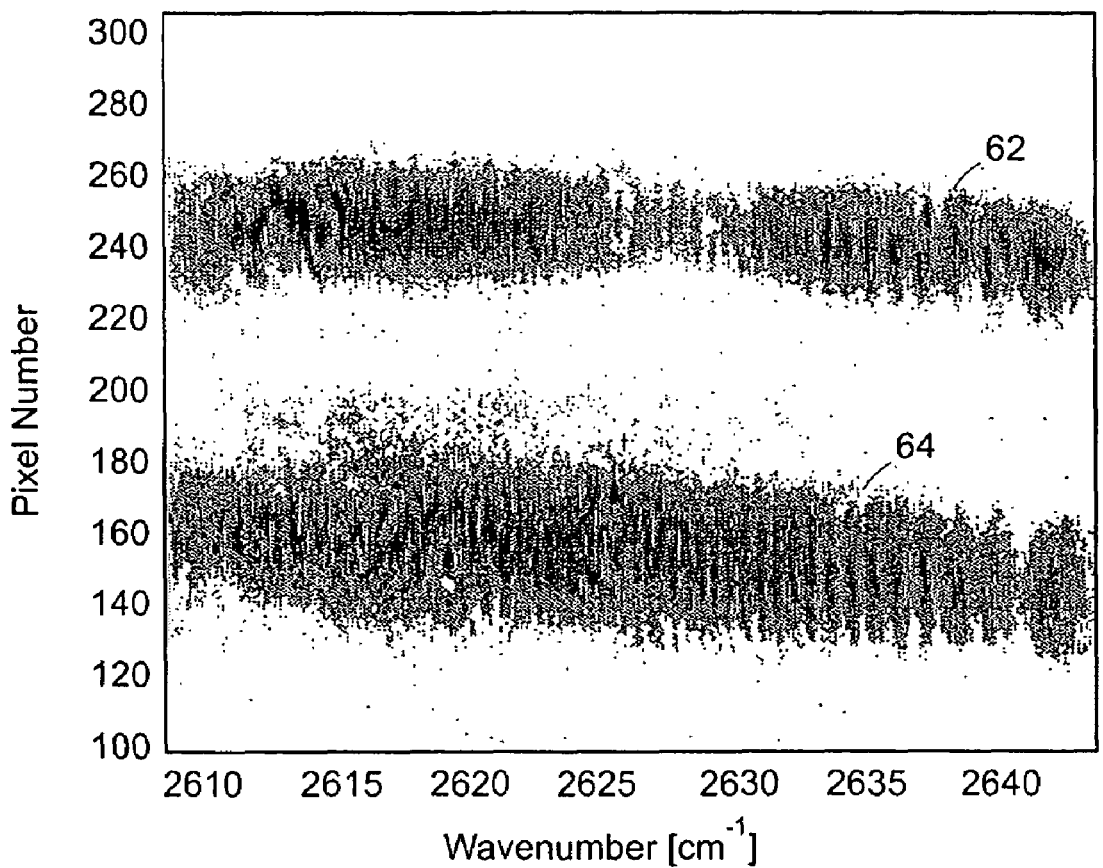

FIG. 8(*b*) shows a single frame image from the CCD for two independent IR spectra taken simultaneously. The upper stripe 62 shows the spectrum of an IR pulse transmitted through acetonitrile, whereas the bottom stripe 64 shows the spectrum of the undisturbed IR pulse. Acetonitrile has a weak absorption line at 2627 $cm^{-1}$ (FWHM ~20 $cm^{-1}$). The SFG spectrometer 5 shows a clear absorption maximum at 2627 $cm^{-1}$ in the upper stripe, correctly corresponding to the acetonitrile resonance.

Inspecting FIG. 8(*b*) closely, there can be seen evidence of two sources of systematic noise in the SFG signals 62 and 64. First, circular patterns randomly dispersed across the array are caused by CCD defects. Second, diffraction of the optical radiation on the edge of the $KNbO_3$ crystal 44 (see FIG. 1) causes vertical diffraction lines in the upconverted signal 46, leading to spatial distortions of the 800 nm light. In the preferred method of the invention, to minimize the impact of these two defects on the results, the data are convoluted with a two-dimensional Gaussian whose width is 15 pixels in each direction. Because the width of the convolution is much smaller than the focusing limit of the IR, this smoothing does not affect the retrieved spectral information. After normalizing for the spatial profile of the optical pulse and integrating each spectrum separately, a difference spectrum is retrieved. FIG. 8(*a*) shows the raw and smoothed absorption spectrum of the acetonitrile resonance overlain with a trace taken with a commercial Fourier transform infrared spectrometer. Both the peak position and the asymmetric line shape of the absorption are accurately measured.

In one embodiment of the present invention, the disclosed methods are applied specifically to analyzing the spectral characteristics of light transmitted in telecommunication bands in the infrared. It is useful and important for telecommunications companies to characterize their fiber-optic networks as completely and precisely as is feasible. Knowledge of the transmission network is required to ensure that the signal will be transmitted faithfully. For example, companies need to know not only the signal attenuation, but the attenuation as a function of wavelength. Chromatic dispersion is now a limiting factor in many networks. Polarization-mode dispersion and polarization-dependent loss need to be well specified. Return loss of all components has to be known.

One embodiment of the upconversion method according to the invention for analyzing signals relating to telecommunications is configured as depicted in FIG. 1, where in this instance the input signal beam 12 derives from a source of IR light that is within one of the following telecommunications frequency bands:

O-band 1260-1360 nm
E-band 1360-1460 nm
S-band 1460-1530 nm
C-band 1530-1565 nm
L-band 1565-1625 nm
U-band 1625-1675 nm In this embodiment, still referring to FIG. 1, a research sample 70 may optionally comprise one or more components of a telecommunications network, such as transmissive optic materials, which are desired to be analyzed for transmission characteristics and other optical properties. Such a sample 70 may also optionally be a segment of optical fiber, including single-mode or multi-mode fiber. In a further embodiment of a telecommunications signal analysis spectrometer, FIG. 6 and FIG. 7 serve to depict 2D scanning spectroscopic approaches that can be utilized to examine the 2D aspects of the transmitted signal from the telecommunications network components.

The invention can be applied in time-resolved mode with sequential IR pulses focused into the sample in specific geometric configurations that allow the detected resultant signal that radiates from the sample to be deconvolved. For details on the related mathematical data analysis see Fecko et al., *Science*, 301/5640, 1698-1702; the cited reference being herein fully incorporated by reference.

It will further be appreciated by one skilled in the art that the disclosed invention can be utilized with numerous IR source lights and transmitted IR signal beams. Further, it will be appreciated that the disclosed methods and apparatus can be utilized in combination with additional optical detection techniques associated with tunable lasers and multi-wavelength detection, including pulsed Raman spectroscopy and coherent anti-Stokes Raman spectroscopy (CARS).

In one embodiment of the upconversion method according to the invention, a Ti:Sapphire pulse is used for the primary IR pulse beam. In this configuration any one of a group of standard nonlinear crystals (e.g., KNbO3, LiNbO3, and BBO) can be used to up convert 1.0-5.5 μm radiation. Upconversion of longer wavelengths can be accomplished with other crystals (e.g., $AgGaS_2$) using other ultrafast upconversion sources (e.g., near-IR OPA radiation). For instance, upconversion with the near infrared light (1.0-1.6 μm) in BBO based OPAs can be used to upconvert mid- to far-IR light into the near infrared and then detect either with Si or InGaAs based arrays. With the appropriate choice of nonlinear crystals and optics, this SFG technique can be implemented with any commercial IR monochrometer eliminating the need for liquid nitrogen cooled IR arrays.

Preferred embodiments of the invention described herein employ an inexpensive 8-bit video-rate camera, but it will be appreciated that higher-end arrays with kHz data acquisition rates will dramatically improve the signal-to-noise. Further, it will be appreciated that CCDs of the "area array", "scanning linear array", and "scanning area array" type can be utilized, inter alia.

EQUIVALENTS

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims below and as set forth in the claims.

What is claimed is:

1. A method for altering an infrared light pulse, comprising:
   generating a first light pulse in an infrared range;
   frequency-dispersing and spatially-dispersing the first light pulse;
   directing a second light pulse onto an optical path with the frequency-dispersed and spatially-dispersed first light pulse;
   directing the frequency-dispersed and spatially-dispersed first light pulse and the second light pulse onto a frequency conversion element to generate a frequency converted light signal, the second light pulse spatially overlapping a spatially distributed bandwidth of the first light pulse at the frequency conversion element;
   separating the second light pulse from the frequency converted light signal; and
   detecting the frequency converted light signal.

2. The method of claim 1, further comprising frequency-dispersing and spatially-dispersing the first light pulse with a grating.

3. The method of claim 1, further comprising detecting the frequency converted signal with a CMOS detector.

4. The method of claim 1, further comprising generating the second light pulse with pulse duration in the range between 1 femtosecond and 10 picoseconds.

5. The method of claim 1, further comprising processing spectral data with a data processor.

6. The method of claim 1, further comprising detecting the signal with a charge coupled device.

7. The method of claim 1, further comprising controlling a light source and the detector with an interface controller.

8. The method of claim 1, further comprising converting an infrared frequency to a higher frequency with a sum frequency generation crystal.

9. The method of claim 8, further comprising using a crystal having a nonlinear optical response such as $KNbO_3$.

10. The method of claim 1, further comprising directing a second broadband light pulse onto the optical path in which the frequency conversion element is positioned with a dielectric mirror.

11. The method of claim 1, further comprising directing the second light pulse to the frequency conversion element with a first reflective element.

12. The method of claim 1, further comprising directing the second light pulse after the frequency conversion element from the optical path with a second reflective element.

13. The method of claim 12, further comprising filtering the frequency converted signal with a bandpass filter having a visible cutoff wavelength.

14. The method of claim 13, wherein the reflecting element has a reflective cutoff wavelength greater than the bandpass filter.

15. The method of claim 1, further comprising calibrating the spectrometer with an interferometer.

16. The method of claim 1, further comprising simultaneously detecting a plurality of frequency-converted signals.

17. The method of claim 16, further comprising forming a spectroscopic image with the plurality of detected signals.

18. The method of claim 1, further comprising monitoring a chemical process.

19. The method of claim 1, further comprising monitoring an optical communication signal such as a fiber optic signal.

20. The method of claim 1, further comprising using an objective lens or cylindrical lens system to direct the first light pulse onto a material.

21. An apparatus for altering an infrared light pulse, comprising:
   a first infrared light pulse source,
   a frequency-dispersing and spatially-dispersing element optically coupled to the first infrared light pulse source,
   a frequency conversion element, and
   a second light pulse source optically coupled to the frequency-conversion element such that light from the second light pulse source overlaps a spatially dispersed bandwidth of a dispersed light signal from the first infrared light pulse source at the frequency conversion element;
   said frequency-dispersing and spatially-dispersing element being positioned to couple the first light pulse source to the frequency-conversion element to generate a frequency-converted optical pulse in the visible light range; and
   a detector that detects the frequency-converted optical pulse.

22. The apparatus of claim 21, wherein the frequency-dispersing and spatially-dispersing element is a grating.

23. The apparatus of claim 21, further comprising a 2D detector array that detects the frequency converted optical pulse.

24. The apparatus of claim 21, wherein the second light pulse source is a source for light pulses in the range between 1 femtosecond and 10 picoseconds in duration.

25. The apparatus of claim 21, wherein the frequency-conversion element is a nonlinear crystal.

26. The apparatus of claim 21, wherein the frequency-dispersing and spatially-dispersing element is a prism or curved grating.

27. A method for spectroscopy comprising:
   generating a first light pulse;
   spectrally dispersing and spatially dispersing the first light pulse;
   optically coupling a frequency conversion material to the spectrally dispersed and spatially dispersed first light pulse;
   generating a second light pulse;
   coupling the second light pulse onto the frequency conversion material, the second light pulse being spatially distributed to overlap a bandwidth of the spectrally dispersed and spatially dispersed first light pulse to generate a frequency converted signal; and
   detecting the dispersed frequency converted signal with a two dimensional array (2D) detector.

28. The method of claim 27, further comprising spectrally dispersing and spatially dispersing the first light pulse with a grating.

29. The method of claim 27, further comprising generating at least one of the first light pulse and the second light pulse with a pulse duration in a range between 1 femtosecond and 10 picoseconds.

30. The method of claim 27, further comprising generating a first light pulse in any one of far-infrared range, infrared range, near-infrared range, visible range, ultraviolet range, microwave range, or X-ray range.

31. An apparatus for altering an infrared light pulse, comprising:
a first light pulse source that emits a narrowband infrared light pulse;
a frequency dispersing and spatially dispersing element optically coupled to the first light pulse source;
a frequency altering element;
a second light pulse source optically coupled to the frequency altering element to overlap the first light pulse source;
said frequency dispersing and spatially dispersing element being positioned to couple a bandwidth of the first light pulse source to the frequency altering element that overlap a spatially distributed second light pulse, said frequency altering element being configured to generate a frequency converted signal; and
a detector that detects the frequency converted signal.

32. The apparatus of claim 31 wherein the frequency dispersing and spatially dispersing element is positioned between the source of the first light pulse source and the coupling of the first and second light pulse sources.

33. The apparatus of claim 31, wherein the frequency dispersing and spatially dispersing element is a spectral-dispersing element positioned between the source of the first light pulse source and the coupling of the first and second light pulse sources.

34. The apparatus of claim 31, wherein the frequency dispersing and spatially dispersing element is a diffraction grating positioned between the source of the first light pulse source and the coupling of the first and second light pulse sources.

35. The apparatus of claim 31 further comprising:
a lens that focuses a pulse from the first light pulse source onto a material;
at least one additional lens or spherical mirror coupled to the first light pulse source, wherein the frequency dispersing and spatially dispersing element is positioned between the source of the first light pulse source and the coupling of the first and second light pulse sources; and
a two dimensional detector optically coupled to light from the material.

36. An apparatus for spectroscopy comprising:
a first infrared light pulse source optically coupled to a material;
a first spectral dispersing and spatial dispersing element optically coupled to the first light pulse;
a second light pulse source optically coupled to the first light pulse source;
a lens that focuses the first light pulse onto the material;
at least one of an additional lens and a spherical mirror optically coupled to the spectral dispersing and spatial dispersing element;
a frequency upconversion element optically coupled to the first light source and the second light source that provides a frequency converted signal over a bandwidth of the first light pulse; and
a two dimensional detector optically coupled to light from the material.

37. The apparatus of claim 36 wherein the spectral dispersing and spatial dispersing element is a grating.

38. The apparatus of claim 36 wherein the second light pulse comprises light pulses in a range between 1 femtosecond and 10 picoseconds in duration.

39. The apparatus of claim 36 wherein the first light pulse source emits light in an infrared range and the second light pulse is in a visible range.

40. The apparatus of claim 36 wherein the first spectral dispersing and spatial dispersing element is a grating, prism, or other dispersive element.

41. An apparatus for 2D spectroscopy employing an altered infrared light pulse, comprising:
a first infrared light pulse source;
a frequency altering element optically coupled to the first infrared light pulse source;
a disperser arranged to spectrally and spatially disperse an infrared light pulse from the first light pulse source, the infrared light pulse having a bandwidth distributed over an area on a surface of the frequency altering element;
a second light pulse source optically coupled to the frequency altering element such that a second light pulse is distributed over the area on the surface to overlap the entire bandwidth of the infrared pulse; and
a detector optically coupled to the frequency altering element that detects a frequency converted 2D spectroscopic signal.

42. The apparatus of claim 36, wherein the frequency altering element converts an infrared light pulse to a visible light pulse.

43. The apparatus of claim 36, wherein multiple independent spatially-displaced infrared pulses are generated, and the detector detects multiple distinct spectroscopic signals.

44. The apparatus of claim 36, wherein the first infrared pulse source comprises:
an optical system that focuses a probe pulse on at least a portion of a sample to provide an infrared signal pulse.

45. The apparatus of claim 44, further comprising:
a raster apparatus that probes the sample with incoming optical pulses in the x and y dimensions.

46. The apparatus of claim 44, further comprising:
an optical apparatus that focuses the probe pulse along at least one dimension to provide a line image of the sample.

47. The apparatus of claim 46, wherein one dimension of the 2D spectroscopic signal is wavelength and another dimension is a spatial dimension of the probe pulse.

* * * * *

UNITED STATES PATENT AND TRADEMARK OFFICE
CERTIFICATE OF CORRECTION

| | | |
|---|---|---|
| PATENT NO. | : 7,696,479 B2 | Page 1 of 1 |
| APPLICATION NO. | : 11/446588 | |
| DATED | : April 13, 2010 | |
| INVENTOR(S) | : Matthew F. DeCamp | |

It is certified that error appears in the above-identified patent and that said Letters Patent is hereby corrected as shown below:

Please delete the paragraph titled 'STATEMENT REGARDING FEDERALLY SPONSORED RESEARCH OR DEVELOPMENT' encompassing Column 1, line 16:

"N/A"

and replace with:

--This invention was made with government support under Grant No. DE-FG02-99ER14988 awarded by the Department of Energy. The government has certain rights in this invention.--

Signed and Sealed this
Twenty-third Day of October, 2012

David J. Kappos
*Director of the United States Patent and Trademark Office*